(12) United States Patent (10) Patent No.: US 12,626,359 B2

Yamamura (45) Date of Patent: May 12, 2026

(54) IMAGE ANALYZER AND STORAGE MEDIUM

(71) Applicant: KONICA MINOLTA, INC., Tokyo (JP)

(72) Inventor: Takuya Yamamura, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 693 days.

(21) Appl. No.: 17/992,386

(22) Filed: Nov. 22, 2022

(65) Prior Publication Data

US 2023/0186466 A1 Jun. 15, 2023

(30) Foreign Application Priority Data

Dec. 13, 2021 (JP) ................................ 2021-201376

(51) Int. Cl.
| | |
|---|---|
| *G06T 7/00* | (2017.01) |
| *A61B 5/0205* | (2006.01) |
| *A61B 6/50* | (2024.01) |

(52) U.S. Cl.
CPC .......... *G06T 7/0012* (2013.01); *A61B 5/0205* (2013.01); *A61B 6/50* (2013.01); *G06T 2207/30061* (2013.01)

(58) Field of Classification Search
None
See application file for complete search history.

(56) References Cited

U.S. PATENT DOCUMENTS

| | | | |
|---|---|---|---|
| 9,064,302 | B2 | 6/2015 | Muraoka et al. |
| 10,271,739 | B2 | 4/2019 | Freeman et al. |
| 10,888,218 | B2 | 1/2021 | Wang |
| 11,129,536 | B2 | 9/2021 | Freeman et al. |
| 11,730,907 | B2 | 8/2023 | Matsutani |
| 2018/0228458 | A1 | 8/2018 | Katsuhara et al. |
| 2020/0327665 | A1* | 10/2020 | Shimamura ............ A61B 6/541 |

FOREIGN PATENT DOCUMENTS

| | | | |
|---|---|---|---|
| JP | 2016179187 A | | 10/2016 |
| JP | 2017018681 A | * | 1/2017 |
| JP | 2018512918 A | | 5/2018 |
| JP | 2018130264 A | | 8/2018 |
| JP | 2020062394 A | | 4/2020 |
| JP | 2020168176 A | | 10/2020 |
| WO | 2012026145 A1 | | 3/2012 |

OTHER PUBLICATIONS

Gosangi et al, COVID-19 ARDS: a review of imaging features and overview of mechanical ventilation and its complications; Oct. 26, 2021.*

(Continued)

*Primary Examiner* — Fan Zhang

(74) *Attorney, Agent, or Firm* — Holtz, Holtz & Volek PC

(57) ABSTRACT

An image analyzer includes a hardware processor that acquires an image obtained by performing still image capturing or dynamic imaging of a subject at least while wearing a ventilator or within a predetermined time after removing the ventilator and generates information regarding presence or absence of complications related to the ventilator of the subject based on the acquired image.

16 Claims, 11 Drawing Sheets

CARDIOTHORACIC RATIO

| | |
|---|---|
| BEFORE WEARING VENTILATOR (9/7) | 45% |
| WHILE WEARING VENTILATOR (9/8) | 55% |
| WHILE WEARING VENTILATOR (9/15) | 45% |

BEFORE WEARING VENTILATOR (9/7)

WHILE WEARING VENTILATOR (9/8)

WHILE WEARING VENTILATOR (TODAY 9/15)

(56) References Cited

OTHER PUBLICATIONS

Baki et al, Feasibility of vocal fold abduction and adduction assessment using cine-MRI, Apr. 16, 2016.*

Mohammed et al, Laryngeal ultrasound as a bedside tool in detecting postextubation stridor in patients with respiratory illness, Feb. 5, 2020.*

Shweel et al; Radiological evaluation of post-traumatic tracheal stenosis using multidetector CT with multiplanar reformatted imaging and virtual bronchoscopy: Comparison with intraoperative findings; May 13, 2013.*

Japanese Office Action (and an English language translation thereof) dated Mar. 4, 2025, issued in counterpart Japanese Application No. 2021-201376.

Imanaka, Hideaki, Respiratory Management Recent Advances Non-invasive Positive Pressure Ventilation and Intubated Positive Pressure Ventilation, 3) Practice of Intubated Positive Pressure Ventilation, c. Key points of systemic management and measures against complications during ventilation, Medical Clinics of Japan, 2004, 1352-1355.

Serita, Akimichi, "Careful management of the artificial airway, 5. Post-extubation complications", Respiratory Care, 2012, 98-103.

Japanese Office Action (and an English language translation thereof) dated Oct. 7, 2025, issued in counterpart Japanese Application No. 2021-201376.

* cited by examiner

FIG.1

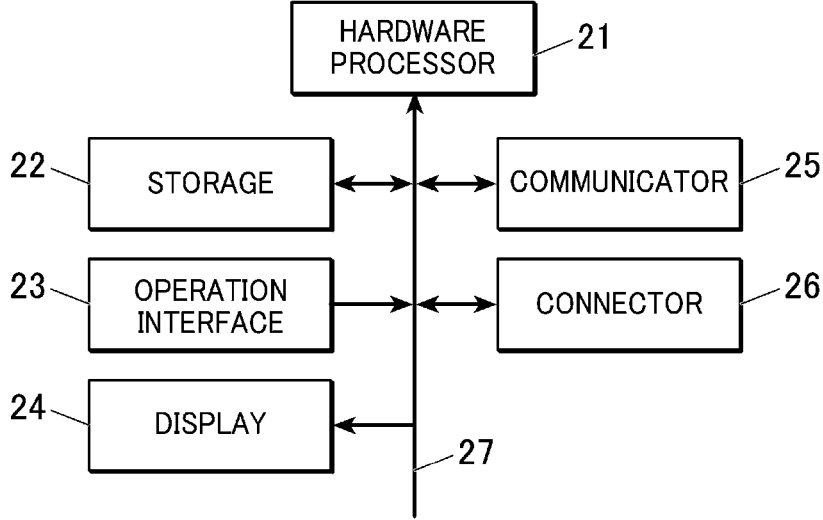

FIG.2

```
        ┌──────────────────┐
        │    HARDWARE      │───21
        │    PROCESSOR     │
        └────────┬─────────┘
                 │
22─┌──────────────┐      ┌──────────────┐
   │   STORAGE    │◄────►│ COMMUNICATOR │───25
   └──────────────┘      └──────────────┘

23─┌──────────────┐      ┌──────────────┐
   │  OPERATION   │◄────►│  CONNECTOR   │───26
   │  INTERFACE   │      └──────────────┘
   └──────────────┘

24─┌──────────────┐
   │   DISPLAY    │◄────
   └──────────────┘      ───27
```

WHEN SPEAKING                                    WHEN NOT SPEAKING

NORMAL                                                ABNORMAL

53

53

EXHALE INHALE

FIG.7

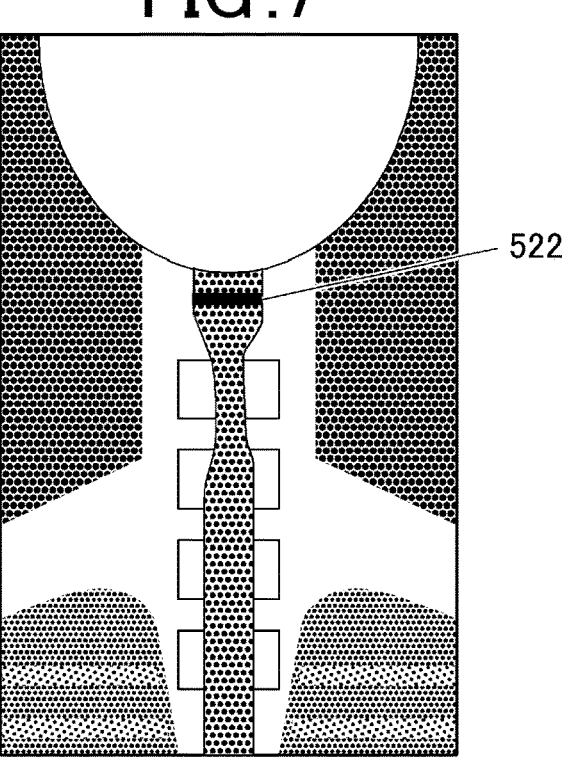

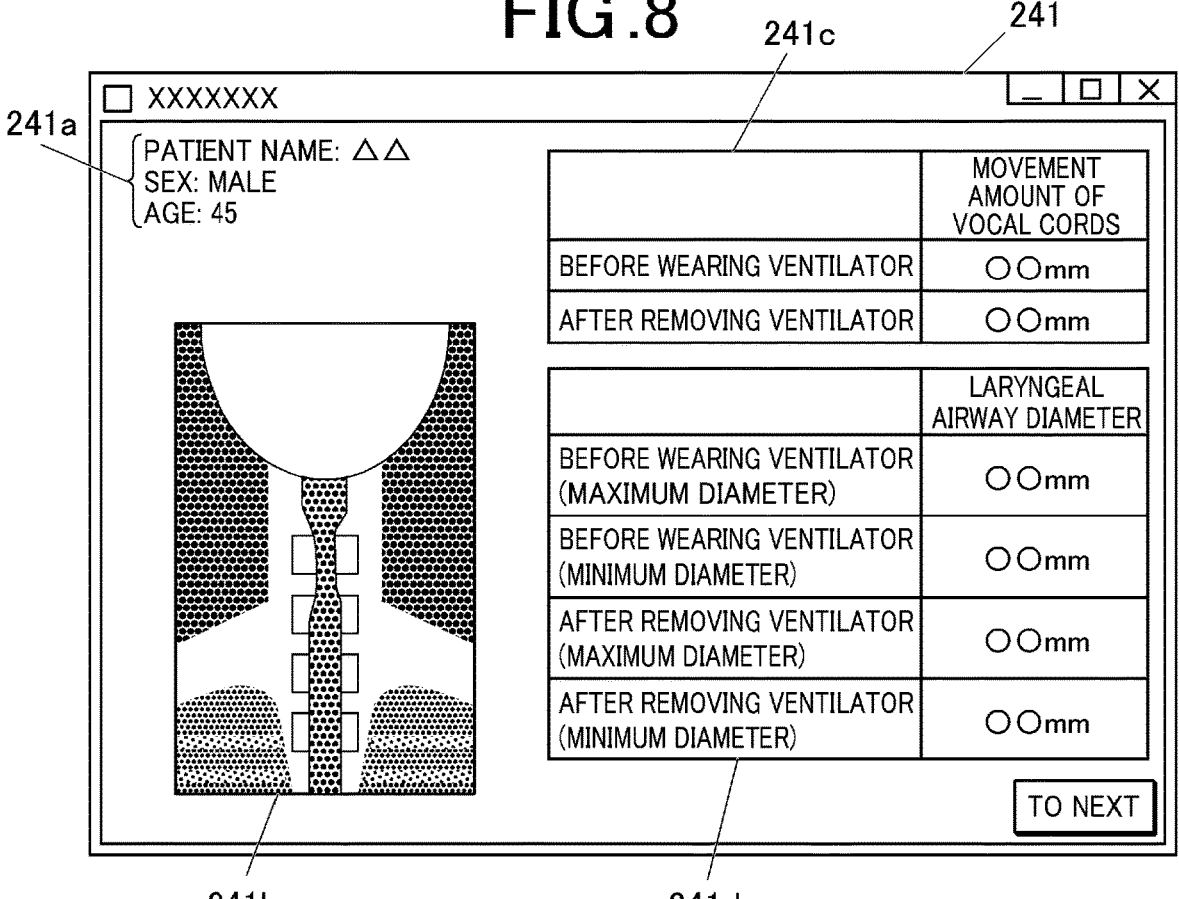

241

241c

241a

PATENT NAME: △△
SEX: MALE
AGE: 45

|  | MOVEMENT AMOUNT OF VOCAL CORDS |
|---|---|
| BEFORE WEARING VENTILATOR | ○○mm |
| AFTER REMOVING VENTILATOR | ○○mm |

|  | LARYNGEAL AIRWAY DIAMETER |
|---|---|
| BEFORE WEARING VENTILATOR (MAXIMUM DIAMETER) | ○○mm |
| BEFORE WEARING VENTILATOR (MINIMUM DIAMETER) | ○○mm |
| AFTER REMOVING VENTILATOR (MAXIMUM DIAMETER) | ○○mm |
| AFTER REMOVING VENTILATOR (MINIMUM DIAMETER) | ○○mm |

TO NEXT 241b          241d

FIG.10

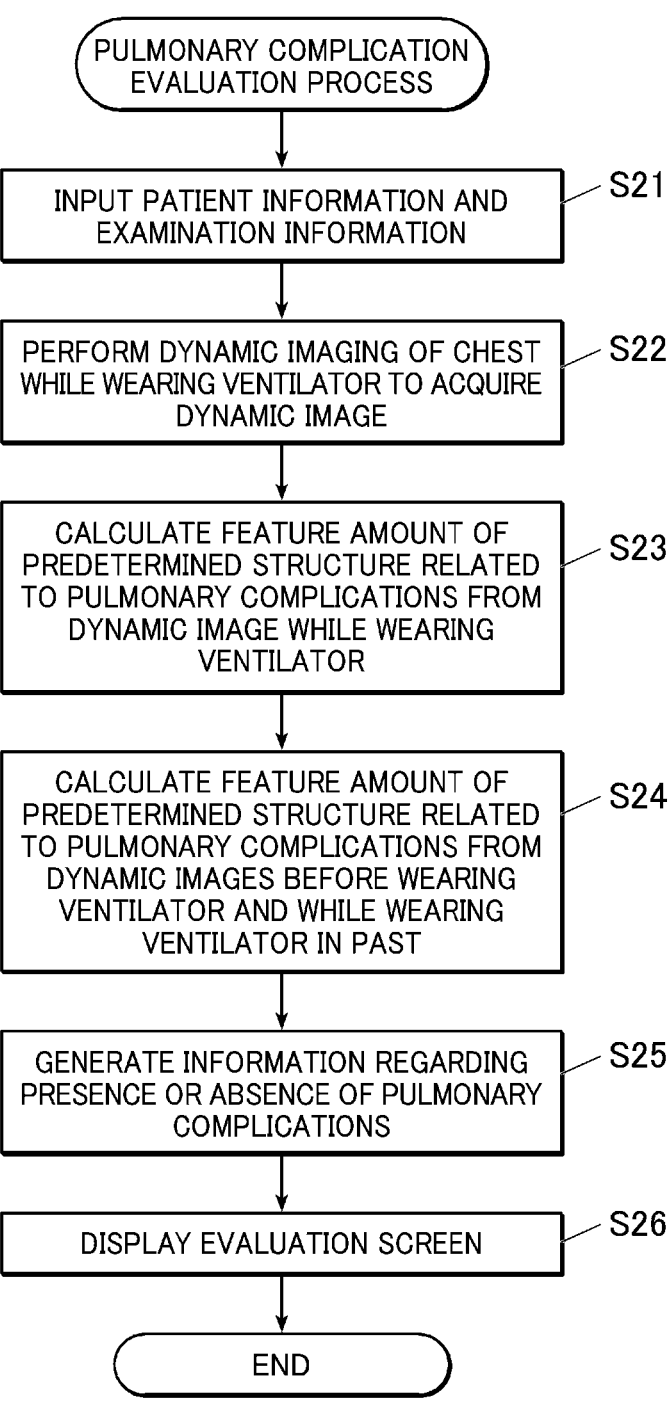

PULMONARY COMPLICATION
EVALUATION PROCESS

INPUT PATIENT INFORMATION AND
EXAMINATION INFORMATION    S21

PERFORM DYNAMIC IMAGING OF CHEST
WHILE WEARING VENTILATOR TO ACQUIRE
DYNAMIC IMAGE    S22

CALCULATE FEATURE AMOUNT OF
PREDETERMINED STRUCTURE RELATED
TO PULMONARY COMPLICATIONS FROM
DYNAMIC IMAGE WHILE WEARING
VENTILATOR    S23

CALCULATE FEATURE AMOUNT OF
PREDETERMINED STRUCTURE RELATED
TO PULMONARY COMPLICATIONS FROM
DYNAMIC IMAGES BEFORE WEARING
VENTILATOR AND WHILE WEARING
VENTILATOR IN PAST    S24

GENERATE INFORMATION REGARDING
PRESENCE OR ABSENCE OF PULMONARY
COMPLICATIONS    S25

DISPLAY EVALUATION SCREEN    S26

END

FIG.13

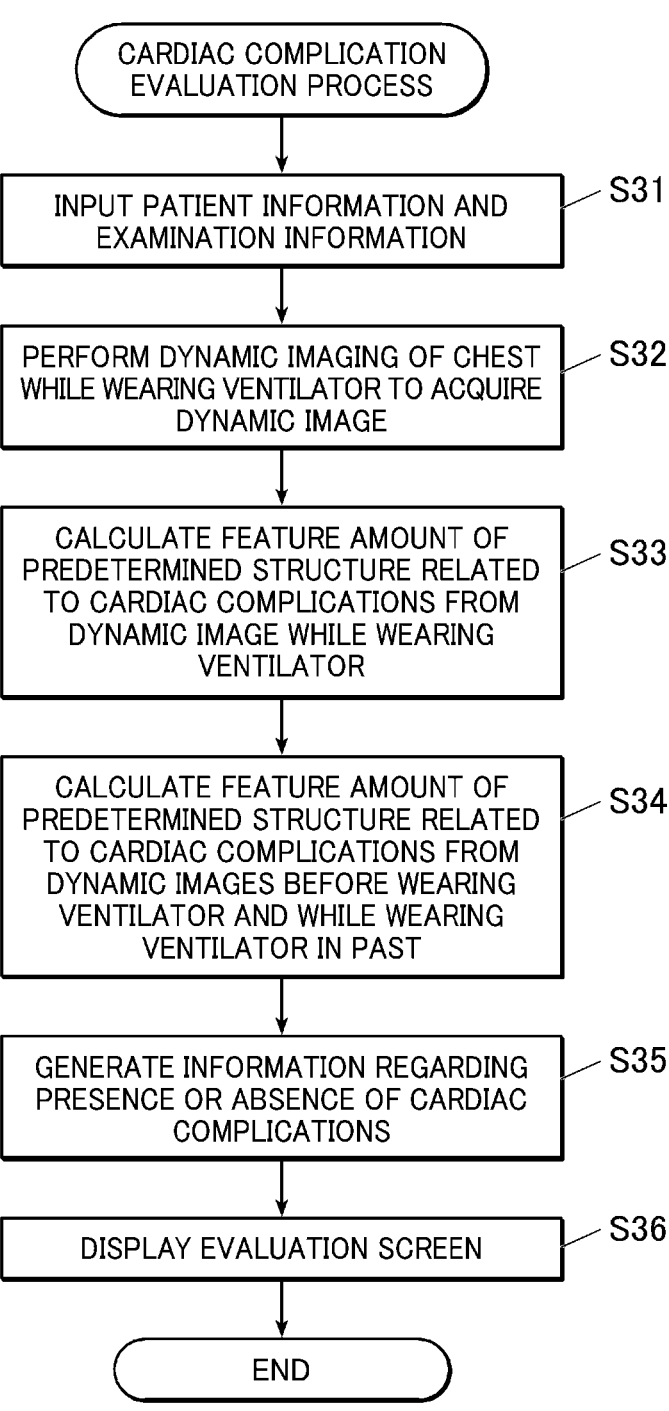

CARDIAC COMPLICATION
EVALUATION PROCESS

INPUT PATIENT INFORMATION AND
EXAMINATION INFORMATION — S31

PERFORM DYNAMIC IMAGING OF CHEST
WHILE WEARING VENTILATOR TO ACQUIRE
DYNAMIC IMAGE — S32

CALCULATE FEATURE AMOUNT OF
PREDETERMINED STRUCTURE RELATED
TO CARDIAC COMPLICATIONS FROM
DYNAMIC IMAGE WHILE WEARING
VENTILATOR — S33

CALCULATE FEATURE AMOUNT OF
PREDETERMINED STRUCTURE RELATED
TO CARDIAC COMPLICATIONS FROM
DYNAMIC IMAGES BEFORE WEARING
VENTILATOR AND WHILE WEARING
VENTILATOR IN PAST — S34

GENERATE INFORMATION REGARDING
PRESENCE OR ABSENCE OF CARDIAC
COMPLICATIONS — S35

DISPLAY EVALUATION SCREEN — S36

END

Figure 14:
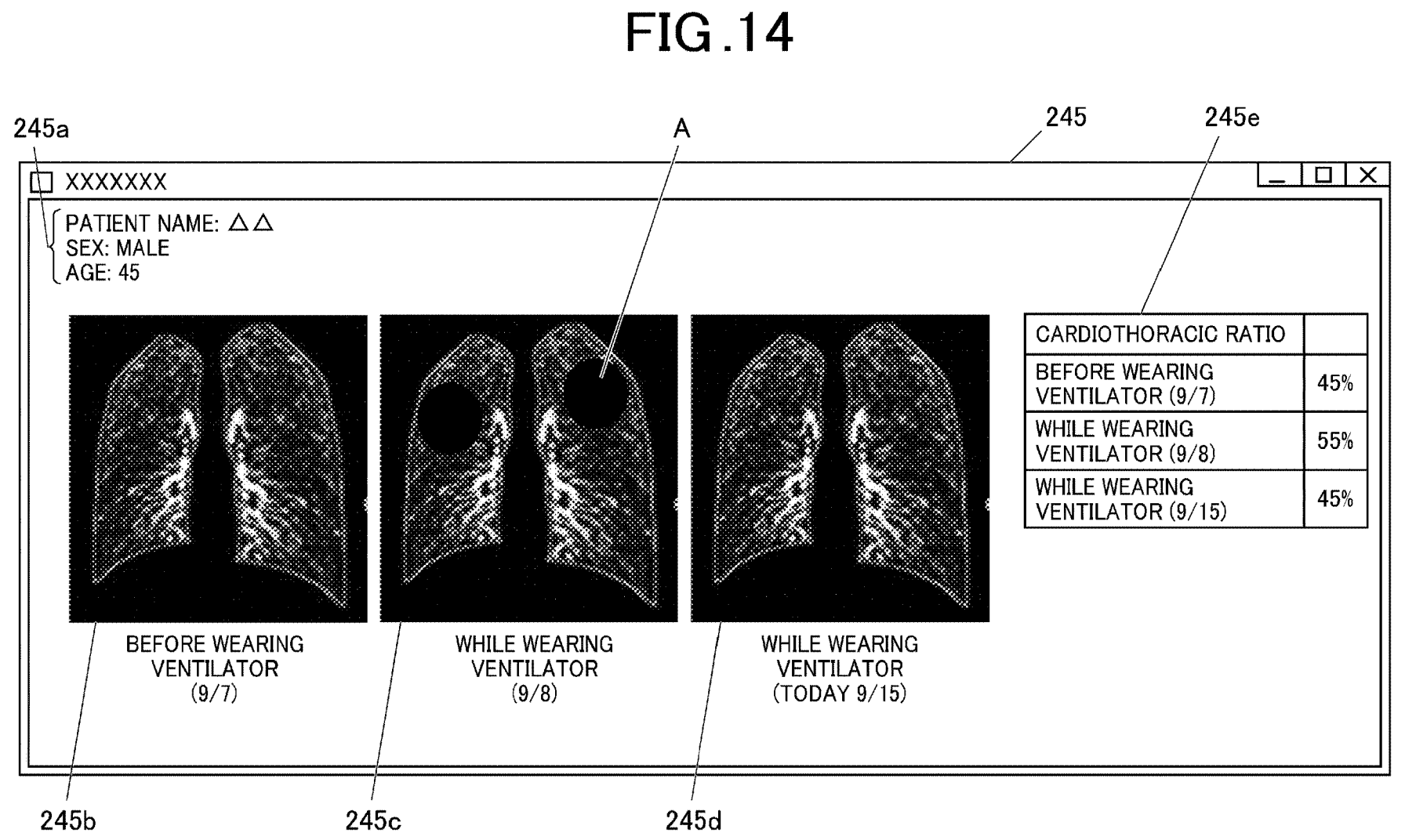

XXXXXXX

PATENT NAME: △△
SEX: MALE
AGE: 45

A

245

245e

| CARDIOTHORACIC RATIO | |
|---|---|
| BEFORE WEARING VENTILATOR (9/7) | 45% |
| WHILE WEARING VENTILATOR (9/8) | 55% |
| WHILE WEARING VENTILATOR (9/15) | 45% |

BEFORE WEARING VENTILATOR (9/7)

245b

WHILE WEARING VENTILATOR (9/8)

245c

WHILE WEARING VENTILATOR (TODAY 9/15)

245d

IMAGE ANALYZER AND STORAGE MEDIUM

CROSS-REFERENCE TO RELATED APPLICATIONS

The entire disclosure of Japanese Patent Application No. 2021-201376 filed on Dec. 13, 2021 is incorporated herein by reference in its entirety.

BACKGROUND

Technological Field

The present disclosure relates to an image analyzer and a storage medium.

Description of the Related Art

A technique has been proposed in which the amount of morphological change in a predetermined structure of the chest is calculated based on a plurality of frame images showing the movements of the chest, which are obtained by radiographically imaging the chest of a subject wearing a ventilator, and the respiratory state of the subject when the ventilator is worn or when the ventilator is removed is evaluated based on the calculated amount of morphological change (see, for example, JP 2018-130264 A).

SUMMARY

Incidentally, there is a risk of complications when a ventilator is worn, but there is no mention of complications in JP 2018-130264 A.

An object of the present disclosure includes assisting a user in appropriately determining whether or not there is a complication due to wearing a ventilator.

To achieve at least one of the abovementioned objects, according to a first aspect of the present disclosure, there is provided an image analyzer including a hardware processor that acquires an image obtained by performing still image capturing or dynamic imaging of a subject at least while wearing a ventilator or within a predetermined time after removing the ventilator and generates information regarding presence or absence of complications related to the ventilator of the subject based on the acquired image.

To achieve at least one of the abovementioned objects, according to a second aspect of the present disclosure, there is provided a non-transitory storage medium storing a computer readable program causing a computer to execute: acquiring an image obtained by performing still image capturing or dynamic imaging of a subject at least while wearing a ventilator or within a predetermined time after removing the ventilator; and generating information regarding presence or absence of complications related to the ventilator of the subject based on the acquired image.

BRIEF DESCRIPTION OF THE DRAWINGS

The advantages and features provided by one or more embodiments of the present disclosure will become more fully understood from the detailed description given hereinbelow and the appended drawings which are given by way of illustration only, and thus are not intended as a definition of the limits of the present disclosure, wherein:

FIG. 1 is a diagram showing the overall configuration of a dynamic analysis system according to the present embodiment;

FIG. 2 is a block diagram showing the functional configuration of a console shown in FIG. 1;

FIG. 7 is a diagram showing an example of calculating the airway diameter of the larynx;

FIG. 8 is a diagram showing an example of an evaluation screen displayed on a display in step S6 of FIG. 6;

FIG. 10 is a flowchart showing a pulmonary complication evaluation process performed by the hardware processor shown in FIG. 2;

FIG. 13 is a flowchart showing a cardiac complication evaluation process performed by the hardware processor shown in FIG. 2; and FIG. 14 is a diagram showing an example of the evaluation screen displayed on the display in step S36 of FIG. 13.

DETAILED DESCRIPTION OF THE EMBODIMENTS

Figure 3:
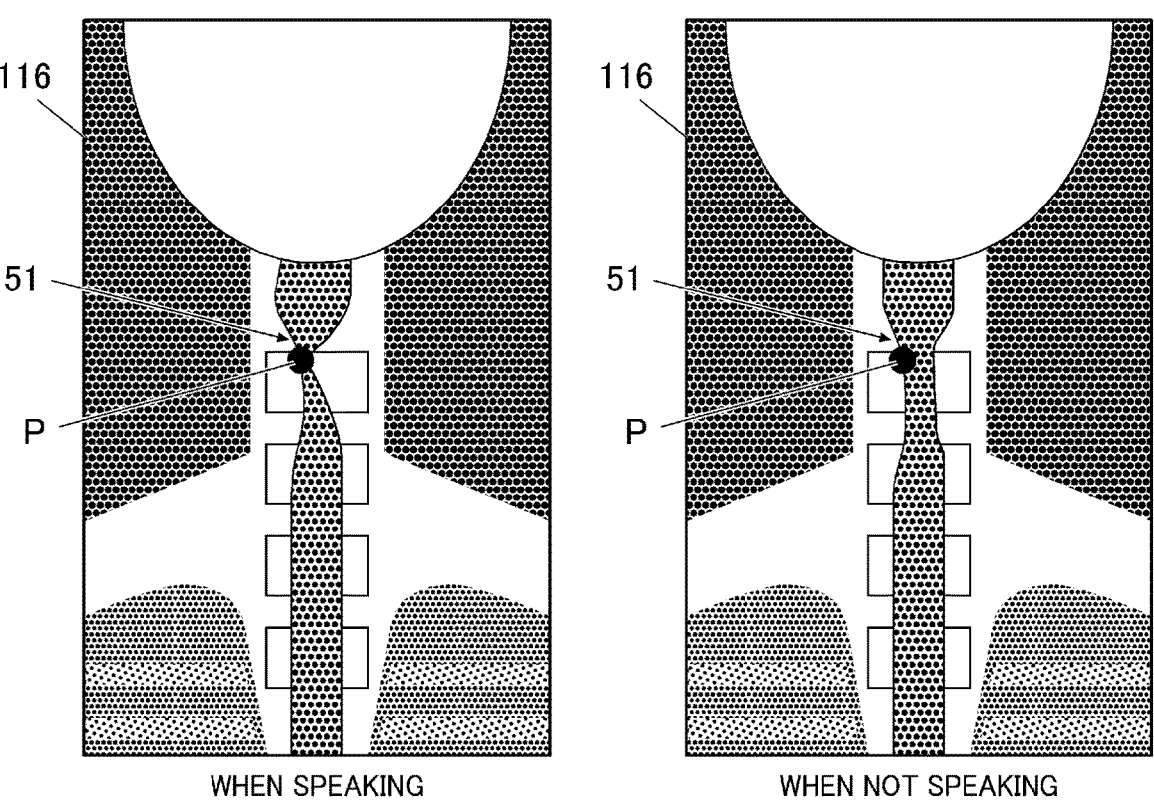
FIG. 3 is a diagram schematically showing the movements of vocal cords in a radiographic image of the airway (front view)

Hereinafter, one or more embodiments of the present disclosure will be described with reference to the drawings. However, the scope of the present disclosure is not limited to the disclosed embodiments or illustrated examples.
(Configuration of a Dynamic Analysis System 100)

First, the configuration of an embodiment according to the present disclosure will be described.

FIG. 1 shows an example of the overall configuration of the dynamic analysis system 100 according to the present embodiment.

The dynamic analysis system 100 is a system for rounds for imaging a patient, who is difficult to move and is in an intensive care unit, an operating room, or the like, as a subject, and includes a radiation generator 1, a console 2, an access point 3, and a flat panel detector (FPD) cassette 4. The radiation generator 1 has wheels, and is configured as a movable medical vehicle in which the console 2 or the access point 3 is installed. In the dynamic analysis system 100, the console 2 can communicate with the radiation generator 1 and the FPD cassette 4 through the access point 3.

As shown in FIG. 1, the dynamic analysis system 100 is a system that is brought into an operating room (intensive care unit) Rc or the like and performs dynamic imaging or still image capturing of a subject H by emitting radiation from a portable radiation source 11 of the radiation generator 1, for example, in a state in which the FPD cassette 4 is placed between the subject H lying on a bed B and the bed B or inserted into an insertion port (not shown) provided on a surface of the bed B opposite to the subject H.

The dynamic imaging refers to acquiring a plurality of images by repeatedly emitting radiation, such as X-rays, to the subject H in a pulsed manner at predetermined time intervals (pulse irradiation) or by continuously emitting radiation to the subject S at a low dose rate without interruption (continuous irradiation). A series of images obtained by dynamic imaging are called a dynamic image. Each of the plurality of images forming the dynamic image is called a frame image.

The dynamic imaging includes moving image capturing, but does not include capturing a still image while displaying a moving image. The dynamic image includes a moving image, but does not include an image obtained by capturing a still image while displaying a moving image.

Hereinafter, each device forming the dynamic analysis system 100 will be described.

The radiation generator 1 includes the radiation source 11 that emits radiation, a radiation exposure controller 12, an exposure switch 13, and the like.

The radiation source 11 emits radiation (X-rays) to the subject H under the control of the radiation exposure controller 12.

The radiation exposure controller 12 controls the radiation source 11 based on the radiation exposure conditions transmitted from the console 2 to perform radiographic imaging (dynamic imaging or still image capturing). The radiation exposure conditions input from the console 2 include, for example, tube current, tube voltage, radiation exposure time, frame rate (the number of frame images captured per unit time (1 second)), total imaging time per imaging or the total number of captured frame images, and additional filter type.

When the exposure switch 13 is pressed, a radiation exposure instruction signal is input to the console 2.

The console 2 outputs radiation exposure conditions according to the input examination information to the radiation generator 1 and outputs image reading conditions to the FPD cassette 4 to control radiation exposure and radiographic image reading operations, or as an image analyzer, analyzes radiographic images (dynamic images or still images) transmitted from the FPD cassette 4 and generates and displays information regarding the presence or absence of complications related to the ventilator of the subject H.

FIG. 2 shows an example of the functional configuration of the console 2. As shown in FIG. 2, the console 2 includes a hardware processor 21, a storage 22, an operation interface 23, a display 24, a communicator 25, a connector 26, and the like, and these are connected to each other through a bus 27.

The hardware processor 21 includes a central processing unit (CPU), a random access memory (RAM), and the like. The CPU of the hardware processor 21 reads a system program or various processing programs stored in the storage 22 according to the operation of the operation interface 23, loads the programs to the RAM, and centrally controls the operation of each unit of the console 2 or the operations of the radiation generator 1 and the FPD cassette 4 according to the loaded programs. The hardware processor 21 performs various processes including an airway complication evaluation process, a pulmonary complication evaluation process, and a cardiac complication evaluation process, which will be described later, according to the loaded programs.

The storage 22 is a non-volatile semiconductor memory, a hard disk, or the like. The storage 22 stores various programs executed by the hardware processor 21, parameters necessary for the execution of processing by the programs, or data such as processing results. For example, the storage 22 stores programs for performing an airway complication evaluation process, a pulmonary complication evaluation process, and a cardiac complication evaluation process, which will be described later. Various programs are stored in the form of readable program codes, and the hardware processor 21 sequentially performs operations according to the program codes.

The storage 22 stores radiation exposure conditions and image reading conditions at the time of dynamic imaging. The radiation exposure conditions and the image reading conditions can be set by the user by operating the operation interface 23.

The storage 22 stores the radiographic image transmitted from the FPD cassette 4 in association with patient information (attribute information) of the subject H at the time of imaging, examination information (examination date, part to be examined (for example, chest or airway), type of imaging (dynamic imaging/still image capturing), timing of imaging (for example, before wearing a ventilator, while wearing a ventilator, or after removing a ventilator)), evaluation items (for example, airway complications, pulmonary complications, . . . ), the calculated feature amount, the generated information regarding the presence or absence of complications, and the like.

The storage 22 may store statistical data of calculation results obtained by calculating the feature amount of a predetermined structure calculated in the airway complication evaluation process, which will be described later, from the radiographic images of healthy subjects.

The operation interface 23 includes a keyboard having cursor keys, letter input keys, various function keys, and the like and a pointing device, such as a mouse, and outputs an instruction signal input by a key operation or a mouse operation on the keyboard to the hardware processor 21. The operation interface 23 may include a touch panel on the display screen of the display 24. In this case, the operation interface 23 outputs an instruction signal input through the touch panel to the hardware processor 21.

The display 24 is, for example, a liquid crystal display (LCD) monitor or a cathode ray tube (CRT) monitor, and displays input instructions, data, and the like from the operation interface 23 according to instructions of display signals input from the hardware processor 21.

The communicator 25 includes a wireless LAN adapter and the like, and controls transmission and reception of data to and from external devices such as the radiation generator 1 and the FPD cassette 4 connected to a communication network such as a wireless LAN through the access point 3.

The connector 26 is a connector for communication connection with the FPD cassette 4 through a cable (not shown).

Returning to FIG. 1, the access point 3 relays communication between the radiation generator 1 and the console 2, communication between the console 2 and the FPD cassette 4, and the like.

The FPD cassette 4 is a portable radiation detector for dynamic imaging. The FPD cassette 4 is formed by arranging a plurality of radiation detecting elements, which detect radiation emitted from the radiation source 11 and transmitted through at least the subject H according to its intensity and convert the detected radiation into an electrical signal and accumulate the electrical signal, in a matrix (in a two-dimensional manner) at a predetermined position on a substrate, such as a glass substrate. A switching element such as a thin film transistor (TFT) is connected to each radiation detecting element, and the switching element controls the accumulation and reading of electrical signals in and to each radiation detecting element to acquire image data (frame images). FPDs include an indirect conversion type in which radiation is converted into an electrical signal by a photoelectric conversion element through a scintillator and a direct conversion type in which radiation is directly converted into an electrical signal, and either type may be used.

The FPD cassette 4 includes a reading controller for controlling accumulation and reading of electrical signals by the switching element and a communicator for communication connection with the console 2 through the access point 3 (both not shown). The image reading conditions, such as a frame rate, the number of captured frame images per imaging, and the image size (matrix size), are set by the console 2 through the communicator. The reading controller controls accumulation and reading of electrical signals in and to each radiation detecting element by the switching element based on the set image reading conditions. The FPD cassette 4 has a connector, and can be connected to the console 2 for communication through a cable (not shown).

The FPD cassette 4 may be brought by a person who performs imaging, such as a radiographer. However, since the FPD cassette 4 is relatively heavy and may break or malfunction if dropped, the FPD cassette 4 can be transported by being inserted into a cassette pocket 61a provided in the medical vehicle.

(Operation of the Dynamic Analysis System 100)

Next, an operation of the dynamic analysis system 100 will be described.

Complications may occur when a ventilator is worn. Complications that can occur when a ventilator is worn include airway complications, pulmonary complications, and cardiac complications.

In the console 2 of the present embodiment, information regarding the presence or absence of airway complications, information regarding the presence or absence of pulmonary complications, and information regarding the presence or absence of cardiac complications can be generated based on radiographic images (dynamic images or still images) obtained by dynamic imaging or still image capturing while wearing a ventilator or after removing a ventilator.

Hereinafter, processing for generating information regarding the presence or absence of each complication will be described.

(Airway Complication Evaluation Process)

The airway complication evaluation process is a process for generating information regarding the presence or absence of airway complications.

Airway complications include vocal cord paralysis, laryngeal edema, and tracheal stenosis.

Vocal cord paralysis is a pathological condition in which the vocal cords remain open and do not close even when speaking. FIG. 3 is a diagram schematically showing the movements of vocal cords in a radiographic image of the airway (front view). Reference numeral 51 in FIG. 3 indicates vocal cords. As shown in FIG. 3, the vocal cords 51 are closed when speaking and widened when not speaking. However, when vocal cord paralysis occurs, the vocal cords remain open.

Figure 4:
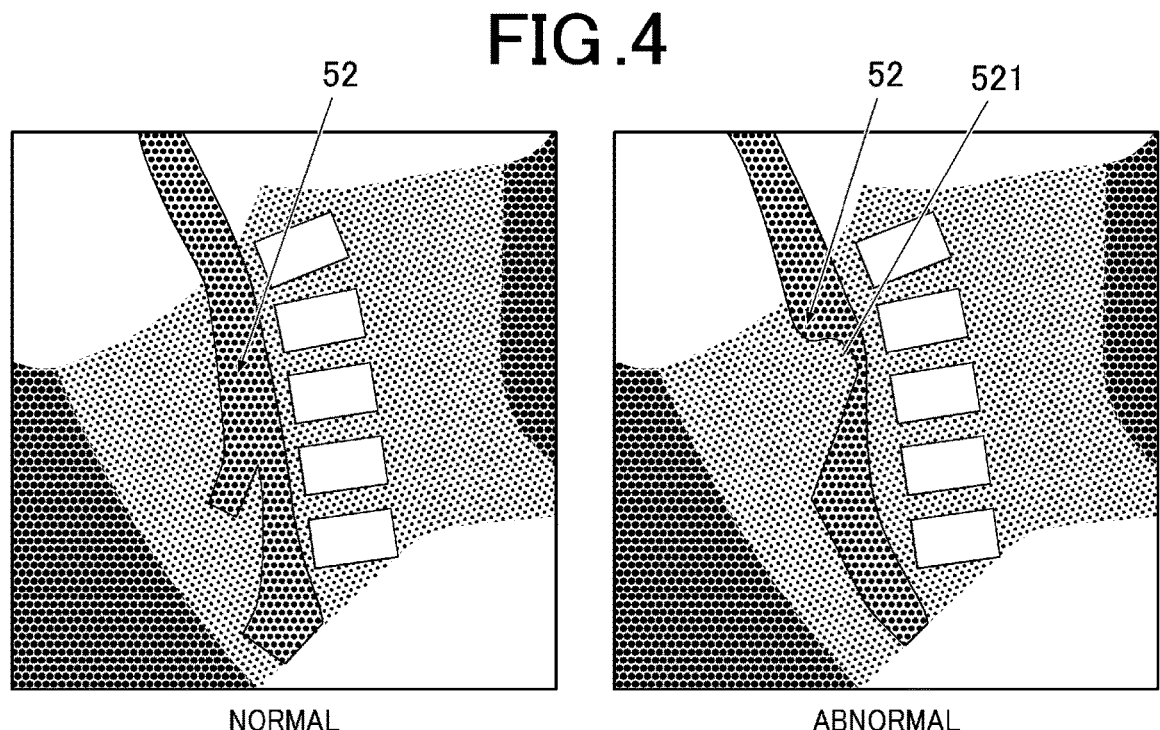
FIG. 4 is a diagram schematically showing a normal larynx and a larynx with laryngeal edema in a radiographic image of the airway (lateral view)

Laryngeal edema is a pathological condition in which the mucous membrane inside the larynx swells to make breathing difficult. FIG. 4 is a diagram schematically showing a normal larynx and a larynx with laryngeal edema (abnormality) in a radiographic image of the airway (lateral view). Reference numeral 52 in FIG. 4 indicates the larynx, and reference numeral 521 indicates laryngeal edema. When laryngeal edema occurs, the larynx becomes compressed and narrower than normal, as shown in FIG. 4.

Figure 5:
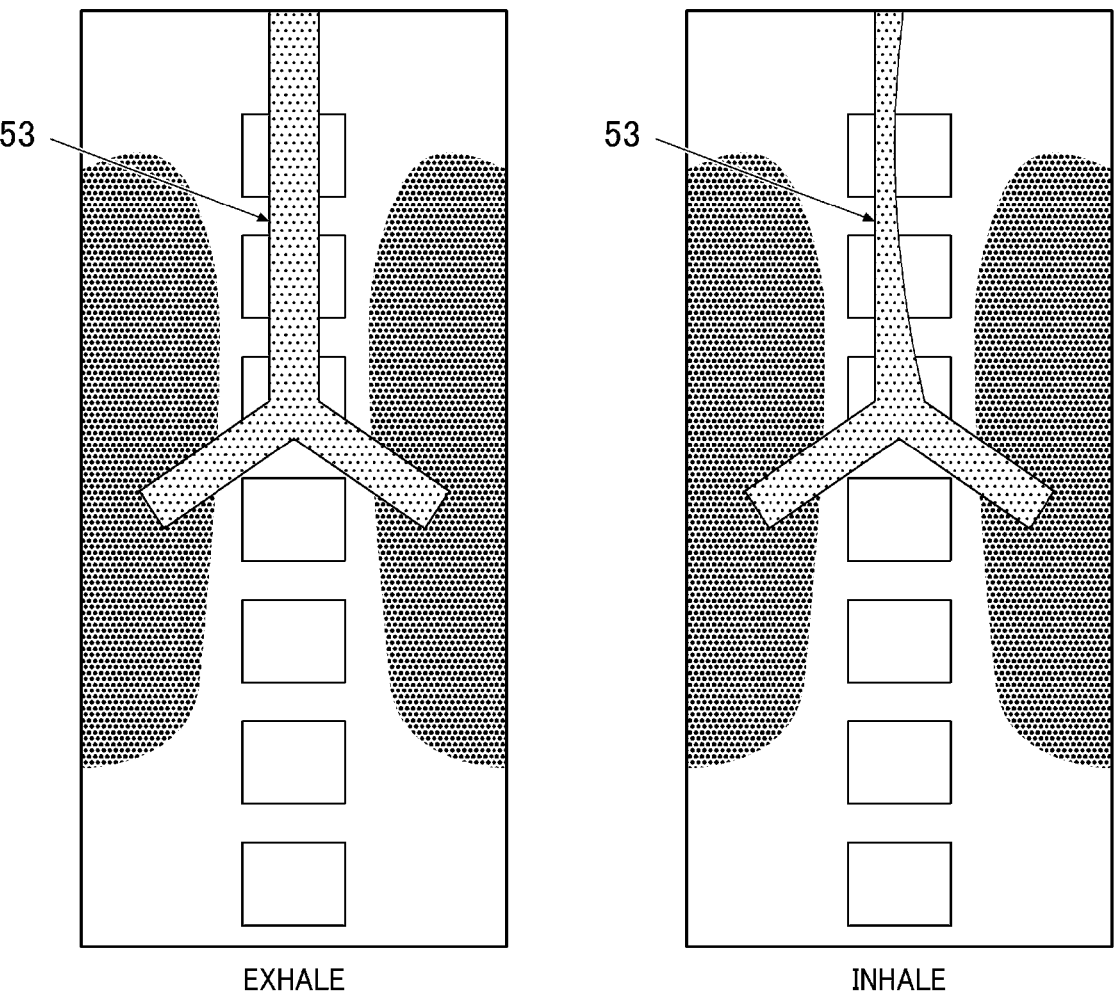
FIG. 5 is a diagram schematically showing the trachea at the time of exhalation and inhalation in a radiographic image of the airway (front view) of a patient with tracheal stenosis.

Tracheal stenosis is a pathological condition in which the diameter of the trachea becomes narrow during inhalation and the diameter of the trachea changes between exhalation and inhalation. FIG. 5 is a diagram schematically showing the trachea at the time of exhalation and inhalation in a radiographic image of the airway (front view) of a patient with tracheal stenosis. Reference numeral 53 in FIG. 5 indicates the trachea.

Since the airway is widened by the tube while the ventilator is being worn, it is difficult to determine airway complications unless the ventilator is removed.

Therefore, in the present embodiment, the airway complication evaluation process is performed within a predetermined time after the removal of a ventilator to generate information regarding airway complications.

Figure 6:
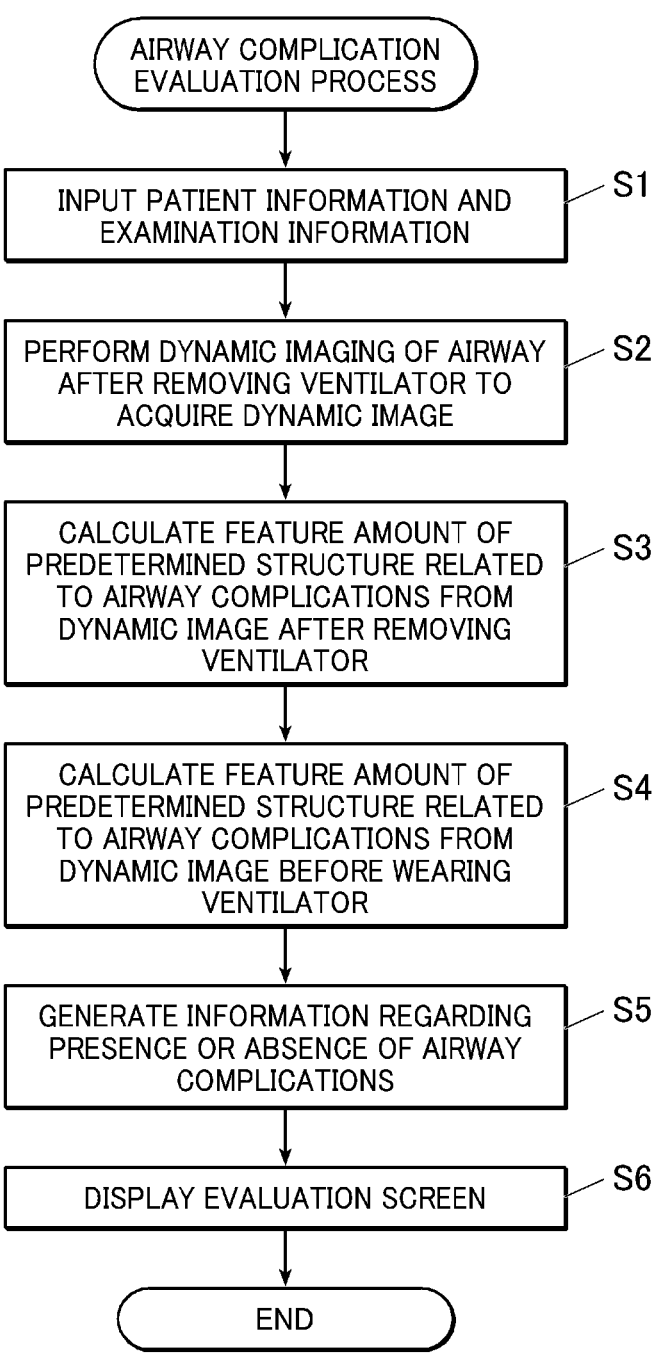
FIG. 6 is a flowchart showing an airway complication evaluation process performed by a hardware processor shown in FIG. 2.

FIG. 6 is a flowchart showing the flow of the airway complication evaluation process performed by the console 2. The airway complication evaluation process is performed in cooperation between the hardware processor 21 and the program stored in the storage 22. Hereinafter, the airway complication evaluation process will be described.

In the description of FIG. 6, a case will be described in which dynamic imaging is performed to acquire a dynamic image and information regarding the presence or absence of airway complications is generated based on the acquired dynamic image. In the dynamic analysis system 100, it is assumed that a dynamic image acquired by dynamic imaging of the airway of the subject H before wearing the ventilator is stored in the storage 22.

First, the hardware processor 21 receives patient information (name, age, sex, disease, and the like) of the subject H and examination information (part to be examined (here, for example, airway), type of imaging (here, dynamic imaging), timing of imaging (here, after removing a ventilator), and evaluation items (here, airway complications)) through the operation interface 23 (step S1).

Then, the hardware processor 21 controls the radiation exposure controller 12 and the FPD cassette 4 based on the input examination information so that dynamic imaging is performed so as to include the airway of the subject H in response to the pressing of the exposure switch 13 and a dynamic image of the airway of subject H after removing the ventilator is acquired (step S2).

Then, the hardware processor 21 calculates a feature amount of a predetermined structure related to airway complications from the acquired dynamic image (step S3).

For example, the hardware processor 21 calculates the amount of movement of the vocal cords or the amount of change in the width of the glottis as the feature amount of the vocal cords. For example, the hardware processor 21 recognizes the vocal cords from each frame image of the acquired dynamic image by using image processing, such as edge detection, or machine learning, and traces a point P (for example, a portion indicated by the point P of the vocal cords 51 in FIG. 3) on the recognized vocal cords from each frame image, and calculates the movement amount (maximum movement amount) of the point P. Alternatively, the width of the glottis may be calculated from each frame image, and the difference between the maximum value and the minimum value may be calculated as the amount of change in the width of the glottis.

For example, as shown in FIG. 7, the hardware processor 21 calculates the airway diameter (indicated by reference numeral 522 in FIG. 7) of the larynx as the feature amount of the larynx. For example, the hardware processor 21 recognizes the larynx from a predetermined frame image of the acquired dynamic image by using image processing, such as edge detection, or machine learning, and calculates the airway diameter of the recognized larynx. Since the larynx extends in the vertical direction, the maximum diameter and the minimum diameter of the larynx may be calculated.

When laryngeal edema occurs, as shown in FIG. 4, the diameter of the laryngeal airway may narrow in the depth direction. In this case, in a radiographic image of the airway captured from the front, the amount of radiation transmitted through a portion of laryngeal edema decreases, so that the signal value (density) of this portion decreases. Therefore, the hardware processor 21 may calculate the signal value (representative value; for example, an average value or a median value) of the larynx as the feature amount of the larynx.

For example, the hardware processor 21 calculates, as the feature amount of the trachea, the amount of movement of the trachea wall or the amount of change in trachea diameter at a predetermined position in the trachea from the larynx to the bronchi. For example, the hardware processor 21 recognizes the airway from a portion below the larynx to the bronchi, as the trachea, from each frame image of the acquired dynamic image by using image processing, such as edge detection, or machine learning, and calculates the amount of movement (maximum movement amount) of the trachea wall at a predetermined position (predetermined position in the vertical direction) of the recognized trachea. Alternatively, the hardware processor 21 may calculate the diameter of the recognized trachea at a predetermined position (predetermined position in the vertical direction) from each frame image and calculate the difference between the maximum value and the minimum value as the amount of change in trachea diameter.

As described above, when tracheal stenosis occurs, the diameter of the trachea changes between exhalation and inhalation. In particular, when the diameter in the depth direction changes, the amount of transmitted radiation changes and accordingly the signal value (density) changes in a radiographic image of the airway captured from the front. Therefore, the hardware processor 21 may calculate the amount of change (signal value change amount) in the signal value (representative value; for example, an average value or a median value) of the trachea as the feature amount of the trachea.

Alternatively, the ratio between the upper airway and the lower airway may be calculated as the feature amount of the trachea.

Then, the hardware processor 21 acquires the feature amount of the predetermined structure related to airway complications from the dynamic image of the airway of the subject H before wearing the ventilator (step S4).

The hardware processor 21 reads the dynamic image of the airway of the subject H before wearing the ventilator from the storage 22, and performs the same processing as described in step S3 on the read dynamic image to acquire the feature amount of the predetermined structure related to airway complications in the dynamic image of the airway of the subject H before wearing the ventilator.

The feature amount of the predetermined structure related to airway complications may be calculated in advance from the dynamic image of the airway of the subject H before wearing the ventilator and stored in the storage 22, so that the feature amount is acquired from the storage 22 in step S4.

Then, the hardware processor 21 generates, as the information regarding the presence or absence of airway complications, information of comparison between the feature amount of the predetermined structure before wearing the ventilator and the feature amount of the predetermined structure after removing the ventilator (step S5).

Then, the hardware processor 21 causes the display 24 to display an evaluation screen 241 on which the generated information regarding the presence or absence of airway complications is displayed (step S6), and ends the airway complication evaluation process.

FIG. 8 is a diagram showing an example of the evaluation screen 241 displayed on the display 24 in step S6. As shown in FIG. 8, for example, patient information 241a of a patient to be evaluated (subject H), a dynamic image 241b acquired in step S2, the feature amount of the vocal cords (here, the movement amount of the vocal cords) 241c before wearing the ventilator and after removing the ventilator, and the feature amount of the larynx (here, the diameter of the laryngeal airway) 241d before wearing the ventilator and after removing the ventilator are displayed on the evaluation screen 241.

Figure 9:
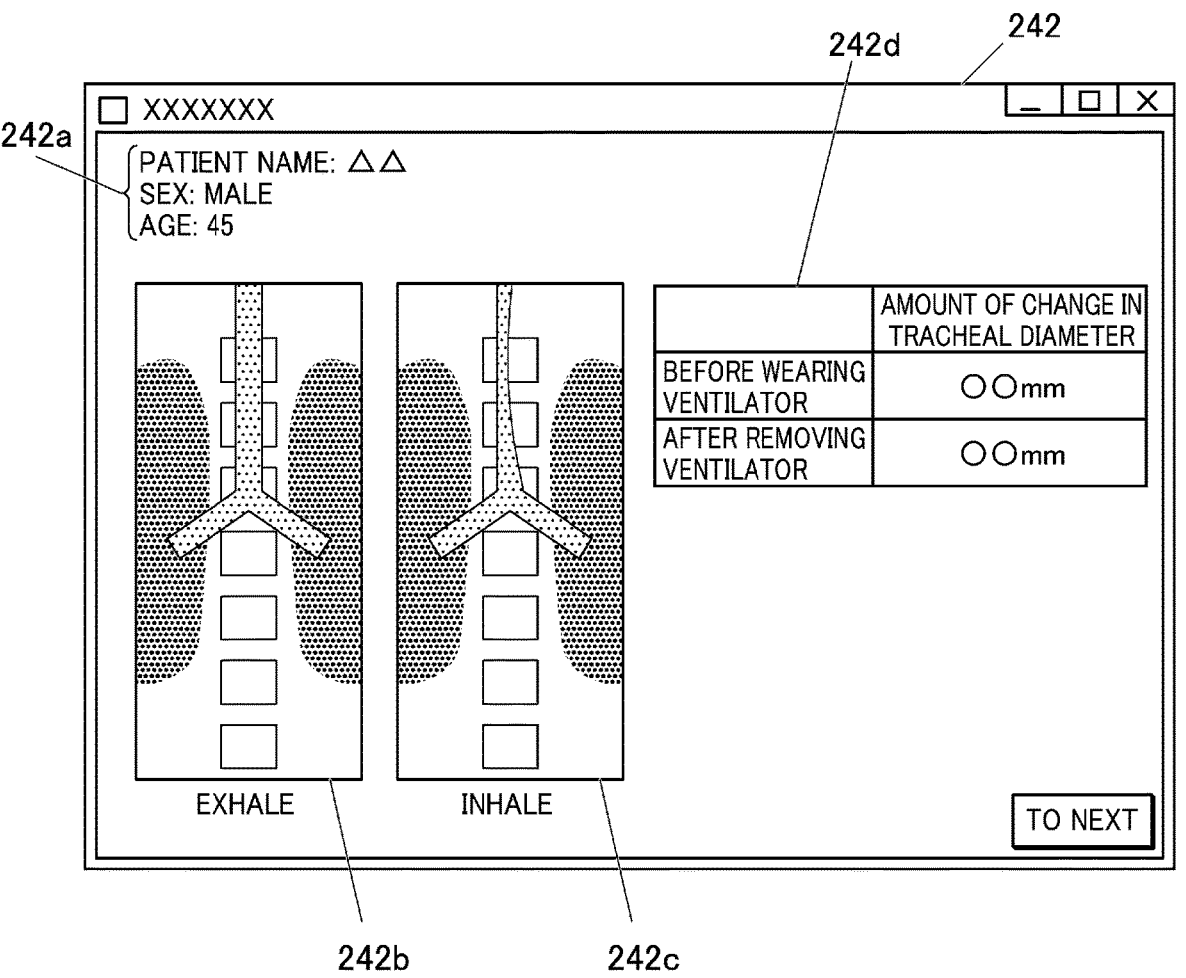
FIG. 9 is a diagram showing an example of the evaluation screen displayed on the display in step S6 of FIG. 6.

FIG. 9 is a diagram showing an example of an evaluation screen 242 displayed on the display 24 in step S6. As shown in FIG. 9, for example, patient information 242a of a patient to be evaluated, a frame image 242b of the maximum exhalation position of the dynamic image acquired in step S2, a frame image 242c of the maximum inhalation position, and feature amounts of the trachea (here, the amount of change in trachea diameter) 242d before wearing the ventilator and after removing the ventilator are displayed on the evaluation screen 242.

As described above, on the evaluation screens 241 and 242, the feature amount (here, the movement amount of the vocal cords, the diameter of the laryngeal airway, and the amount of change in trachea diameter) of the predetermined structure related to airway complications before wearing the ventilator and after removing the ventilator are displayed in a comparable manner as information regarding the presence or absence of airway complications. Therefore, the user can easily grasp the presence or absence of airway complications such as vocal cord paralysis, laryngeal edema, and tracheal stenosis.

In the evaluation screen 241, as the dynamic image 241b, the dynamic image acquired in step S2 may be displayed as a moving image, or only the representative frame image may be displayed. Dynamic images (or representative frame images) before wearing the ventilator and after removing the ventilator may be displayed side by side, or dynamic images (or representative frame images) may be displayed with annotations added to a portion where the movement amount of the vocal cords or the diameter of the airway diameter is measured.

In the airway complication evaluation process described above, dynamic imaging of the airway is performed, and the obtained dynamic image is analyzed to generate information regarding the presence or absence of complications related to the ventilator. However, it is also possible to capture the still image of the airway and analyze the obtained still image to generate information regarding the presence or absence of complications related to the ventilator.

For example, laryngeal edema does not have any movement. Therefore, the signal value of the laryngeal airway diameter or the laryngeal region can be calculated from a still image obtained by still image capturing of the airway of the subject H after removing the ventilator, and information regarding the presence or absence of complications related to the ventilator can be generated based on a comparison with the signal value of the laryngeal airway diameter or the laryngeal region of the subject H before wearing the ventilator.

For example, the amount of change in tracheal diameter, the amount of movement of the tracheal wall, or the amount of change in the signal value of the trachea can be calculated from a still image during exhalation and a still image during inhalation obtained by still image capturing of the airway of the subject H during exhalation and inhalation after removing the ventilator, and information regarding the presence or absence of complications related to the ventilator (tracheal stenosis) can be generated based on a comparison with the amount of change in tracheal diameter, the amount of movement of the tracheal wall, or the amount of change in the signal value of the trachea during exhalation and inhalation of the subject H before wearing the ventilator.

Laryngeal edema can be detected in both a frontal image of the airway (see FIG. 5) and a lateral image of the airway (see FIG. 4). Therefore, information regarding the presence or absence of complications related to the ventilator may be generated by using either one of the images. When laryngeal edema is suspected based on the result of comparison between the feature amount in one of the images and a threshold value set in advance, the other image may also be used to generate information regarding the presence or absence of complications related to the ventilator (tracheal stenosis).

In the airway complication evaluation process described above, comparison information obtained by comparing the feature amount after removing the ventilator with the feature amount of the same patient before wearing the ventilator is generated as information regarding the presence or absence of complications related to the ventilator. However, the present disclosure is not limited to this, and comparison information obtained by comparing the feature amount after removing the ventilator with statistical data of healthy subjects (for example, statistical data as a calculation result obtained by calculating the feature amount calculated in the airway complication evaluation process from the radiographic images of healthy subjects) may be generated as the information regarding the presence or absence of complications related to the ventilator.

In the airway complication evaluation process described above, for all items of vocal cord paralysis, laryngeal edema, and tracheal stenosis as airway complications, information regarding the presence or absence of complications is generated. However, the user may be able to select which item of information to generate through the operation interface 23.

When the difference between the feature amount after removing the ventilator and the feature amount before wearing the ventilator (or statistical data) exceeds a threshold value set in advance, an alert may be output (display, voice output, and the like).

(Pulmonary Complication Evaluation Process)

The pulmonary complication evaluation process is a process for generating information regarding the presence or absence of pulmonary complications.

Pulmonary complications include pneumothorax, pneumonia, atelectasis, pulmonary edema, and pleural effusion.

These complications occur primarily while wearing a ventilator.

Therefore, in the present embodiment, the pulmonary complication evaluation process is performed while wearing a ventilator to generate information regarding pulmonary complications.

FIG. 10 is a flowchart showing the flow of the pulmonary complication evaluation process performed by the console 2. The pulmonary complication evaluation process is performed in cooperation between the hardware processor 21 and the program stored in the storage 22. Hereinafter, the pulmonary complication evaluation process will be described.

In the description of FIG. 10, a case will be described in which dynamic imaging is performed to acquire a dynamic image and information regarding the presence or absence of pulmonary complications is generated based on the acquired dynamic image. In the dynamic analysis system 100, it is assumed that a dynamic image acquired by dynamic imaging of the chest of the subject H before wearing the ventilator or a dynamic image or a feature amount acquired by the pulmonary complication evaluation process performed while wearing the ventilator in the past is stored in the storage 22.

First, the hardware processor 21 receives patient information (name, age, sex, disease, and the like) of the subject H and examination information (part to be examined (here, for example, chest), type of imaging (here, dynamic imaging), timing of imaging (here, while wearing a ventilator), and evaluation items (here, fore, pulmonary complications)) through the operation interface 23 (step S21).

Then, the hardware processor 21 controls the radiation exposure controller 12 and the FPD cassette 4 based on the input examination information so that dynamic imaging of the chest of the subject H wearing the ventilator is performed in response to the pressing of the exposure switch 13 to acquire a dynamic image (step S22).

Then, the hardware processor 21 calculates a feature amount of a predetermined structure related to pulmonary complications from the acquired dynamic image (step S23).

Among the complications that occur while wearing a ventilator, pneumonia is a condition in which pathogens that have invaded through the airway proliferate in the lungs and cause inflammation. Atelectasis is a condition in which a part or entirety of the lung is depleted of air and collapsed due to any cause that prevents air from reaching the lung tissue. Pulmonary edema is a condition in which fluid in the blood leaks out and accumulates in the alveoli. Pleural effusion is an abnormal accumulation of fluid in the thoracic cavity.

In a radiographic image of a lung field with pneumonia, atelectasis, pulmonary edema, or pleural effusion, the signal value (density) in the lung field is lower than usual. When atelectasis or pleural effusion occurs, the area of the lung field area becomes smaller than usual. Pulmonary edema is often accompanied by cardiomegaly. In this case, the cardiothoracic ratio (the ratio of the width of the heart to the width of the ribcage) is larger than usual.

Therefore, in step S23, for example, the hardware processor 21 calculates at least one of the signal value (representative value; for example, an average value or a median value) of the left and right lung fields, the lung field area, and the cardiothoracic ratio as the feature amount of the predetermined structure related to pulmonary complications.

For example, the hardware processor 21 recognizes a lung field region from each frame image of the acquired dynamic image by using known image processing such as edge detection or machine learning, and calculates the lung field area and the signal value (representative value; for example, an average value or a median value) of each of the left and right lung field regions. Then, for example, the signal value and the representative value (for example, a maximum value, a minimum value, or an average value) of the lung field area calculated from each frame image are set as feature amounts. The hardware processor 21 recognizes a cardiac region from a predetermined frame image of the acquired dynamic image (for example, a frame image of the maximum inhalation position) by using known image processing such as template matching or machine learning, and calculates a cardiothoracic ratio.

The hardware processor 21 stores the calculated feature amount in the storage 22 in association with the patient information, the examination information, and the dynamic image.

On the other hand, in the case of pneumothorax, the lung field shrinks in the thoracic cavity. Therefore, it is necessary to recognize the lung field region in the thoracic cavity. However, in general lung field region recognition, the inside of the contour of the thoracic cavity is recognized as a lung field region.

Figure 12:
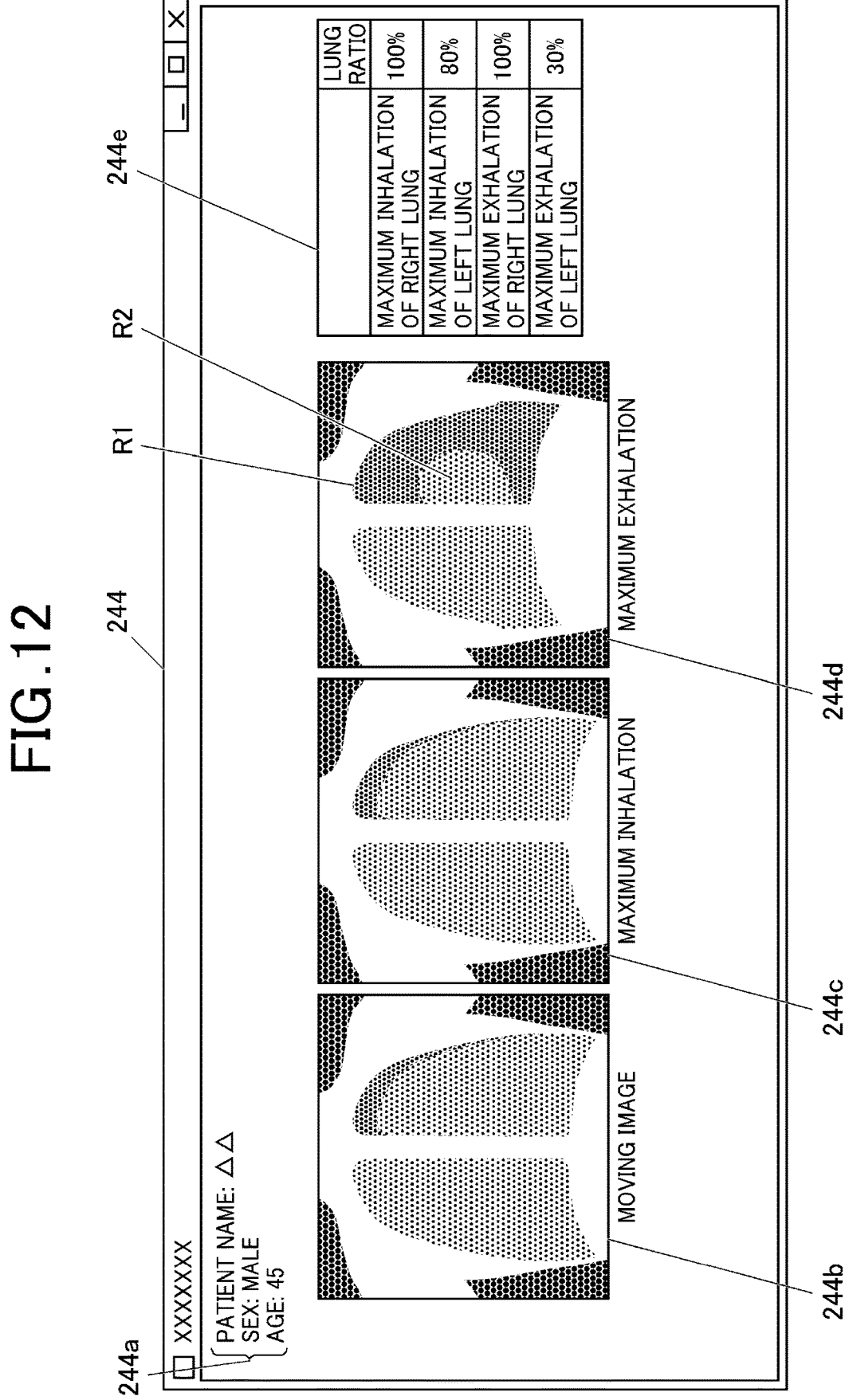
FIG. 12 is a diagram showing an example of the evaluation screen displayed on the display in step S26 of FIG. 10.

Therefore, the hardware processor 21 performs frequency enhancement processing for enhancing high frequency components on each frame image of the dynamic image, generates an image from which the ribs are removed, and recognizes a first lung field region (a region surrounded by the contour of the thoracic cavity) (see R1 in FIG. 12). The hardware processor 21 performs edge detection or the like in the recognized first lung field region to recognize a second lung field region (see R2 in FIG. 12) surrounded by the visceral pleura. Then, information regarding the size of each of the left and right lung fields or the amount of change thereof, for example, the ratio of the area of the second lung field region to the area of the first lung field region (area within the outline of the thoracic cavity) recognized from the frame image of the maximum exhalation position and the frame image of the maximum inhalation position (referred to as a lung ratio) is calculated for each of the left and right lungs and set as a feature amount.

Then, the hardware processor 21 acquires the feature amount of the predetermined structure related to pulmonary complications in the dynamic image captured before wearing the ventilator and the dynamic image captured while wearing the ventilator in the past (step S24).

The hardware processor 21 reads, from the storage 22, a dynamic image of the subject H captured before wearing the ventilator and a dynamic image of the subject H captured while wearing the ventilator in the past and calculates feature amounts related to pneumonia, atelectasis, pulmonary edema, and pleural effusion described in step S23 for the read dynamic images, thereby acquiring the feature amounts related to pneumonia, atelectasis, pulmonary edema, and pleural effusion of the predetermined structure related to pulmonary complications in the past dynamic image before wearing the ventilator and the dynamic image while wearing the ventilator (in the past).

If the feature amounts related to pneumonia, atelectasis, pulmonary edema, and pleural effusion have already been calculated from the past dynamic images and stored in the storage 22, the feature amounts are acquired from the storage 22 in step S24.

Then, the hardware processor 21 generates information regarding the presence or absence of pulmonary complications based on the feature amounts calculated in steps S23 and S24 (step S25).

For example, the hardware processor 21 stores information indicating a temporal change in at least one of the signal value of the lung field region, the lung field area, and the cardiothoracic ratio before and while wearing the ventilator as information regarding the presence or absence of pneumonia, atelectasis, pulmonary edema, and pleural effusion.

The image before wearing the ventilator and the image while wearing the ventilator (in the past) and the images (moving images or representative frame images) acquired in step S22 may be arranged side by side to generate information regarding the presence or absence of pneumonia, atelectasis, pulmonary edema, and pleural effusion.

Information in which at least the frame images of the maximum exhalation position and the maximum inhalation position acquired in step S22 are subjected to frequency enhancement processing and arranged in a comparable manner and/or information regarding the size of the lung field or the amount of change thereof is generated as information regarding the presence or absence of pneumothorax.

Then, the hardware processor 21 causes the display 24 to display an evaluation screen 241 on which the generated information regarding the presence or absence of pulmonary complications is displayed (step S26), and ends the pulmonary complication evaluation process.

Figure 11:
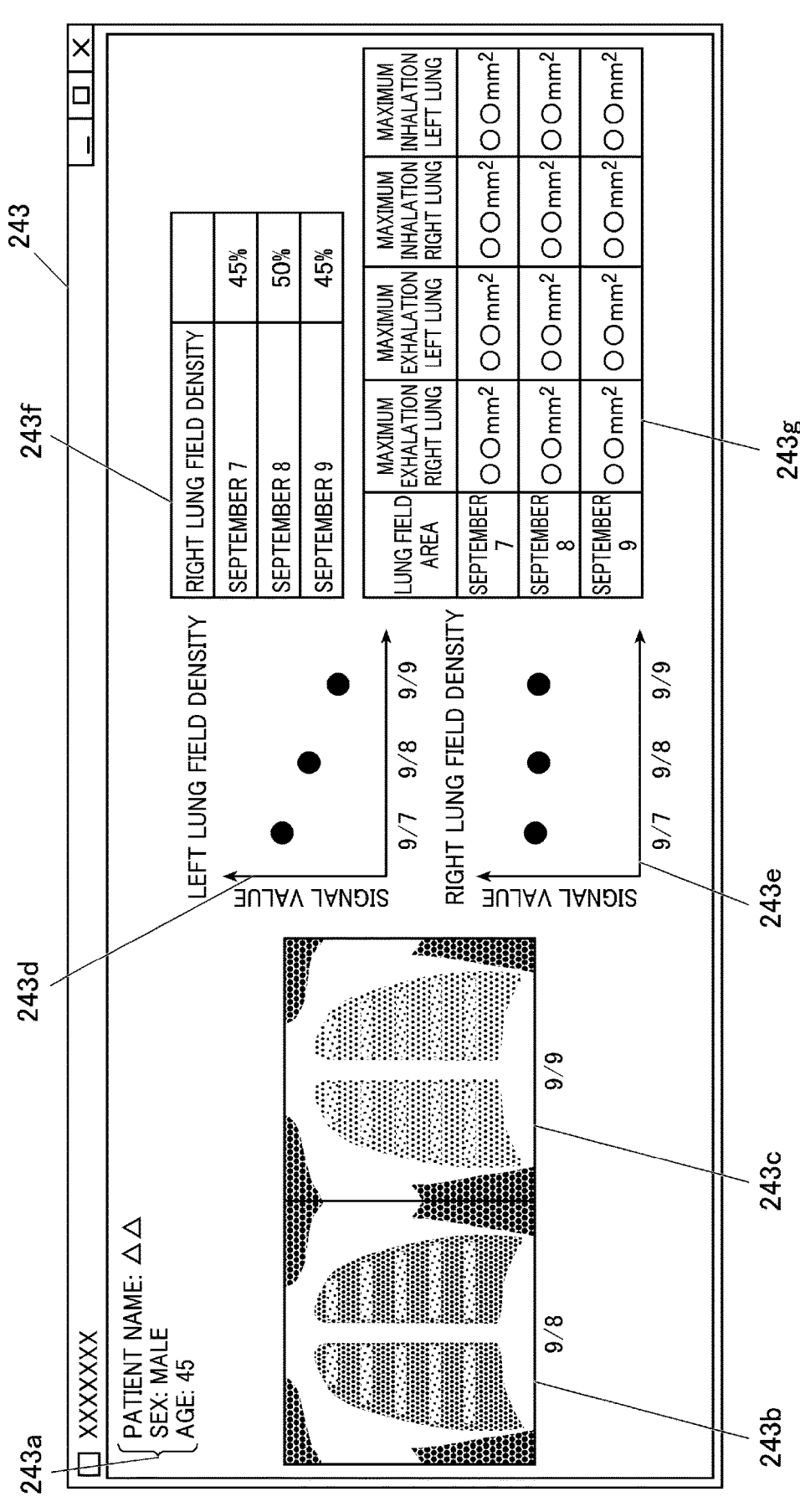
FIG. 11 is a diagram showing an example of the evaluation screen displayed on the display in step S26 of FIG. 10.

FIG. 11 is a diagram showing an example of an evaluation screen 243 displayed on the display 24 in step S26. FIG. 11 shows an example of the evaluation screen 243 on which information regarding the presence or absence of pneumonia, atelectasis, pulmonary edema, and pleural effusion is displayed. As shown in FIG. 11, for example, patient information 243a of a patient to be evaluated, a dynamic image 243b (either a representative frame image or a moving image) acquired before wearing the ventilator or acquired while wearing the ventilator (in the past), a dynamic image 243c captured this time, graphs 243d and 243e showing temporal changes in the signal values of the left and right lung fields, a table 243f showing a temporal change in the cardiothoracic ratio, and a table 243g showing a temporal change in the lung field area are displayed on the evaluation screen 243.

As described above, on the evaluation screen 243, images from before wearing the ventilator to the present and temporal changes in feature amounts (here, the signal value of the lung field region, the lung field area, and the cardiothoracic ratio) of the predetermined structure related to pulmonary complications are displayed in a comparable manner as information regarding the presence or absence of pulmonary complications. Therefore, the user can easily grasp the presence or absence of pulmonary complications, specifically, pneumonia, atelectasis, pulmonary edema, or pleural effusion. When a complication is being treated, the user can easily grasp whether or not the treatment is effective.

FIG. 12 is a diagram showing an example of an evaluation screen 244 displayed on the display 24 in step S26. FIG. 12 shows an example of the evaluation screen 244 on which information regarding the presence or absence of pneumothorax is displayed. As shown in FIG. 12, for example, patient information 244a of a patient to be evaluated, a frequency-enhanced dynamic image 244b generated in step S23, a frame image 244c of the maximum inhalation position, a frame image 244d of the maximum exhalation position, and a table 244e showing the lung ratios of the maximum exhalation position and the maximum inhalation position of each of the right lung and the left lung are displayed on the evaluation screen 244.

As described above, on the evaluation screen 244, the frame image of the maximum exhalation position and the frame image of the maximum inhalation position while the ventilator is being worn are displayed side by side in a comparable manner as information regarding the presence or absence of pulmonary complications, and the lung ratios of the maximum exhalation position and the maximum inhalation position of each of the right lung and left lung are displayed. Therefore, the user can easily grasp the presence or absence of pneumothorax as a pulmonary complication.

In the pulmonary complication evaluation process described above, dynamic imaging of the chest is performed, and the obtained dynamic image is analyzed to generate information regarding the presence or absence of pulmonary complications. However, it is also possible to capture the still image of the chest and analyze the obtained still image to generate information regarding the presence or absence of pulmonary complication. For example, a still image of the maximum inhalation position (when taking a deep breath) or the maximum exhalation position (when exhaling completely) may be captured, and the captured still image may be analyzed.

In the pulmonary complication evaluation process described above, for all items of pneumothorax, pneumonia, atelectasis, pulmonary edema, and pleural effusion as pulmonary complications, information regarding the presence or absence of complications is generated. However, the user may be able to select which item of information to generate through the operation interface 23.

When the difference between the feature amount calculated before wearing the ventilator or while wearing the ventilator in the past and the feature amount calculated this time exceeds a threshold value set in advance or when the feature amount calculated this time exceeds a threshold value set in advance, an alert may be output (display, voice output, and the like).

The information regarding the presence or absence of pneumothorax may be generated by using an image captured within a predetermined time after the ventilator is removed.

In the pulmonary complication evaluation process, as a preferable example, the information indicating a temporal change between the feature amount calculated from the image captured before wearing the ventilator and the image captured while wearing the ventilator in the past and the feature amount calculated from the image captured this time is set as information regarding the presence or absence of complications. However, information indicating a temporal change between the feature amount calculated from one of the image captured before wearing the ventilator and the image captured while wearing the ventilator in the past and the feature amount calculated from the image captured this time may be set as information regarding the presence or absence of complications.

(Cardiac Complication Evaluation Process)

The cardiac complication evaluation process is a process for generating information regarding the presence or absence of cardiac complications.

Cardiac complications include heart failure. Heart failure as a complication occurs while wearing a ventilator.

Therefore, in the present embodiment, the cardiac complication evaluation process is performed while wearing a ventilator to generate information regarding cardiac complications.

FIG. 13 is a flowchart showing the flow of the cardiac complication evaluation process performed by the console 2. The cardiac complication evaluation process is performed in cooperation between the hardware processor 21 and the program stored in the storage 22. Hereinafter, the cardiac complication evaluation process will be described.

In the description of FIG. 13, a case will be described in which dynamic imaging is performed to acquire a dynamic image and information regarding the presence or absence of cardiac complications is generated based on the acquired dynamic image. In the dynamic analysis system 100, it is assumed that a dynamic image acquired by dynamic imaging of the chest of the subject H before wearing the ventilator or a dynamic image or a feature amount acquired by the cardiac complication evaluation process performed while wearing the ventilator in the past is stored in the storage 22.

First, the hardware processor 21 receives patient information (name, age, sex, disease, and the like) of the subject H and examination information (part to be examined (here, for example, chest), type of imaging (here, dynamic imaging), timing of imaging (here, while wearing a ventilator), and evaluation items (here, fore, cardiac complications)) through the operation interface 23 (step S31).

Then, the hardware processor 21 controls the radiation exposure controller 12 and the FPD cassette 4 based on the input examination information so that dynamic imaging of the chest of the subject H is performed in response to the pressing of the exposure switch 13 to acquire a dynamic image (step S32).

Dynamic imaging of the chest may be the same as in the pulmonary complication evaluation process.

Then, the hardware processor 21 calculates a feature amount of a predetermined structure related to cardiac complications from the acquired dynamic image (step S33).

The heart pumps blood throughout the body like a pump, but heart failure is a condition in which this function is weakened and the necessary blood cannot be supplied to the whole body. In the case of heart failure, necessary blood is not supplied to the lung field and a region with lack of blood flow appears. In the case of heart failure, the cardiothoracic ratio increases.

Therefore, in step S33, for example, the hardware processor 21 performs a blood flow analysis on the acquired dynamic image to calculate a feature amount related to blood flow for each small region (for each pixel or a plurality of pixels) of the lung field region as the feature amount of a predetermined structure related to cardiac complications and calculate the cardiothoracic ratio as the feature amount of a predetermined structure related to cardiac complications. Either one of the feature amounts may be calculated.

As a blood flow analysis method, for example, a difference value (absolute value of the difference value) between the signal value of each small region of the lung field region of each frame image of the dynamic image and the signal value of the corresponding small region of an analysis reference frame image (frame image with the highest signal value (that is, a frame image when the blood flow is the lowest)) that serves as a reference for analysis is calculated as a feature amount indicating the blood flow rate of each small region of the lung field region of each frame image. Alternatively, a difference value between the signal value of each small region of the lung field region of each frame image of the dynamic image and the signal value of the corresponding small region of a frame image adjacent in the time direction may be calculated as a feature amount indicating the blood flow rate of each small region of each frame image. When the dynamic image is an image captured in a respiratory state, it is preferable to calculate the difference value after filtering a temporal change in the signal value for each corresponding small region between frame images with a high-pass filter in the time direction (for example, a cutoff frequency of 0.7 Hz).

Alternatively, for example, as described in JP 2012-239796A, the heart region may be recognized from the dynamic image, the signal value waveform of the heart region may be generated as a heartbeat signal waveform, a signal value waveform may be generated for each small region of the lung field region of the dynamic image, a cross-correlation coefficient with respect to the heartbeat signal waveform may be calculated while shifting the generated signal value waveform by one frame interval (while shifting the generated signal value waveform in the time direction), and the calculated cross-correlation coefficient may be set as a feature amount related to blood flow for each frame image of each small region.

The hardware processor 21 stores the calculated feature amount in the storage 22 in association with the patient information, the examination information, and the dynamic image.

Then, the hardware processor 21 acquires the feature amount of the predetermined structure related to cardiac complications in the dynamic image captured before wearing the ventilator and the dynamic image captured while wearing the ventilator in the past (step S34).

The hardware processor 21 reads the dynamic image of the subject H before wearing the ventilator and the dynamic image of the subject H while wearing the ventilator in the past from the storage 22, and performs the same processing as described in step S33 on the read dynamic images to acquire the feature amount of the predetermined structure related to cardiac complications in the dynamic images before and while wearing the ventilator in the past.

If the feature amount of the predetermined structure related to cardiac complications has already been calculated from the acquired past dynamic images, the feature amount is acquired from the storage 22.

Then, the hardware processor 21 generates information regarding the presence or absence of pulmonary complications (step S35).

For example, in each dynamic image, the maximum value of the feature amount related to blood flow calculated for each frame image is combined into one image to generate analysis result images colored according to the magnitude of the maximum value, and information in which the generated analysis result images are arranged chronologically is generated. A table or a graph showing a temporal change in the cardiothoracic ratio is generated. Only one of these may be generated.

Then, the hardware processor 21 causes the display 24 to display an evaluation screen 245 on which the generated information regarding the presence or absence of cardiac complications is displayed (step S36), and ends the cardiac complication evaluation process.

FIG. 14 is a diagram showing an example of the evaluation screen 245 displayed on the display 24 in step S36. As shown in FIG. 14, for example, patient information 245*a* of a patient to be evaluated, analysis result images 245*b* and 245*c* generated before and while wearing a ventilator (in the past), an analysis result image 245*d* generated by performing imaging this time, and a table 245*f* in which the feature amount (cardiothoracic ratio) calculated from the dynamic images acquired before and while wearing a ventilator (in the past) and the feature amount (cardiothoracic ratio) calculated from the dynamic image captured this time are displayed on the evaluation screen 245.

As shown in FIG. 14, on the evaluation screen 245, images from before wearing the ventilator to the present and temporal changes in feature amounts (here, the feature amount related to blood flow and the cardiothoracic ratio) of the predetermined structure related to cardiac complications are displayed in a comparable manner as information regarding the presence or absence of cardiac complications. Therefore, the user can easily grasp the presence or absence of cardiac complications such as heart failure. When a complication is being treated, the user can easily grasp whether or not the treatment is effective. For example, in FIG. 14, a loss of blood flow (portion indicated by A in FIG. 14) is seen in the analysis result image of 9/8, but no conspicuous loss of blood flow is seen in the analysis result image of this time. Therefore, it can be seen that an improvement is made by the treatment.

In the cardiac complication evaluation process described above, dynamic imaging of the chest is performed, and the obtained dynamic image is analyzed to generate information regarding the presence or absence of cardiac complications. However, the cardiothoracic ratio can be generated by capturing a still image of the maximum exhalation position (when taking a deep breath) of the chest and analyzing the obtained still image.

When the difference between the feature amount calculated before wearing the ventilator or while wearing the ventilator and the feature amount calculated this time exceeds a threshold value set in advance or when the feature amount calculated this time exceeds a threshold value set in advance, an alert may be output (display, voice output, and the like).

In the cardiac complication evaluation process, as a preferable example, the information indicating a temporal change between the feature amount calculated from the image captured before wearing the ventilator and the image captured while wearing the ventilator in the past and the feature amount calculated from the image captured this time is set as information regarding the presence or absence of complications. However, information indicating a temporal change between the feature amount calculated from one of the image captured before wearing the ventilator and the image captured while wearing the ventilator in the past and the feature amount calculated from the image captured this time may be set as information regarding the presence or absence of complications.

Although it is preferable to perform all of the above-described airway complication evaluation process, pulmonary complication evaluation process, and cardiac complication evaluation process, any one or two of these may be performed.

While the embodiment of the present disclosure has been described above, the description in the above embodiment is a preferable example of the dynamic analysis system according to the present disclosure, and the present disclosure is not limited thereto.

For example, in the above embodiment, the case where the dynamic analysis system is a system for rounds has been described as an example, but the present disclosure can also be applied to a dynamic analysis system that performs imaging in the imaging room and analyzes the obtained dynamic image.

In the above description, an example is disclosed in which a hard disk, a semiconductor non-volatile memory, or the like is used as a computer-readable medium for a program according to the present disclosure, but the present disclosure is not limited to this example. As other computer-readable media, a portable recording medium, such as a CD-ROM, can be applied. A carrier wave is also applied as a medium for providing data of the program according to the present disclosure through a communication line.

The detailed configuration and detailed operation of each device provided in the dynamic analysis system can also be appropriately changed without departing from the spirit of the present disclosure.

Although embodiments of the present disclosure have been described and illustrated in detail, the disclosed embodiments are made for purposes of illustration and example only and not limitation. The scope of the present disclosure should be interpreted by terms of the appended claims.

What is claimed is:

1. A dynamic analysis system, comprising:
a radiographic imaging system including a radiation generator that emits radiation and a flat panel detector that detects emitted radiation, the radiographic imaging system being operable to perform radiographic imaging of a subject; and
a hardware processor configured to:
receive order information specifying an evaluation item related to evaluating complications caused by a subject wearing a ventilator; and
execute, in accordance with the received order information, an evaluation process specified by the evaluation item, the evaluation process including at least one of an airway complication evaluation process, a pulmonary complication evaluation process, or a cardiac complication evaluation process,
wherein in executing the evaluation process, the hardware processor is configured to:
control the radiographic imaging system to perform radiographic imaging of the subject to acquire a still or dynamic radiographic image of a target region of the subject at least while wearing a ventilator or within a predetermined time after removing the ventilator, in accordance with the evaluation process specified by the evaluation item;
detect, in the acquired radiographic image, a predetermined anatomical structure related to the specified evaluation process by performing image processing including at least one of edge detection, frequency enhancement, template matching, machine learning, or blood flow analysis;
calculate, based on the performed image processing, a first feature amount of the predetermined structure related to the evaluation process;
acquire a second feature amount of the predetermined structure calculated from a radiographic image of the airway of the same subject captured before the subject was wearing the ventilator, the second feature amount being calculated using the same processing used to calculate the first feature amount;
generate comparison information by comparing the first feature amount with the second feature amount;
generate information regarding presence or absence of complications related to the ventilator of the subject based on the generated comparison information, in accordance with the specified evaluation process;
display an evaluation screen in which the generated information is displayed together with at least the first and second feature amounts and the radiographic image from which the first feature amount was calculated; and
generate and output an audio or visual alert when a difference between the first feature amount and the second feature amount exceeds a threshold value set in advance.

2. The dynamic analysis system according to claim 1, wherein the complications include at least one of an airway complication evaluated in the airway complication evaluation process, a pulmonary complication evaluated in the pulmonary complication evaluation process, or a cardiac complication evaluated in the cardiac complication evaluation process.

3. The dynamic analysis system according to claim 2, wherein the airway complication includes at least one of vocal cord paralysis, tracheal stenosis, or laryngeal edema.

4. The dynamic analysis system according to claim 3, wherein the hardware processor calculates an amount of movement of vocal cords or an amount of change in a width of glottis based on a dynamic image obtained by performing dynamic imaging of an airway of the subject within a predetermined time after removing the ventilator, and generates information regarding presence or absence of vocal cord paralysis of the subject based on the calculated amount of movement of the vocal cords or the amount of change in the width of the glottis.

5. The dynamic analysis system according to claim 4, wherein the hardware processor generates, as the information regarding the presence or absence of vocal cord paralysis, information of comparison between the amount of movement of the vocal cords or the amount of change in the width of the glottis, which is calculated based on the dynamic image obtained by performing dynamic imaging of the airway of the subject within a predetermined time after removing the ventilator, and an amount of movement of the vocal cords or an amount of change in the width of the glottis, which is calculated based on a dynamic image obtained by performing dynamic imaging of the airway of the subject before wearing the ventilator, or statistical data of an amount of movement of vocal cords or an amount of change in a width of glottis in healthy subjects.

6. The dynamic analysis system according to claim 3, wherein the hardware processor calculates an amount of movement of a tracheal wall, an amount of change in a diameter of a trachea, or an amount of change in a signal value of the trachea based on an image obtained by performing still image capturing or dynamic imaging of an airway of the subject within a predetermined time after removing the ventilator, and generates information regarding presence or absence of tracheal stenosis of the subject based on the calculated amount of movement of the tracheal wall, the calculated amount of change in the diameter of the trachea, or the calculated amount of change in the signal value of the trachea.

7. The dynamic analysis system according to claim 6, wherein the hardware processor generates, as the information regarding the presence or absence of tracheal stenosis, information of comparison between the amount of movement of the tracheal wall, the amount of change in the diameter of the trachea, or the amount of change in the signal value of the trachea, which is calculated based on the image obtained by performing still image capturing or dynamic imaging of the airway of the subject within a predetermined time after removing the ventilator, and an amount of movement of the tracheal wall, an amount of change in the diameter of the trachea, or an amount of change in the signal value of the trachea, which is calculated based on the image obtained by performing still image capturing or dynamic imaging of the airway of the subject before wearing the ventilator, or statistical data of an amount of movement of a tracheal wall and an amount of change in a diameter of a trachea in healthy subjects or an amount of change in a signal value of the trachea in radiographic images of healthy subjects.

8. The dynamic analysis system according to claim 3, wherein the hardware processor acquires a laryngeal airway diameter or a signal value of a larynx based on an image obtained by performing still image capturing or dynamic imaging of an airway of the subject within a predetermined time after removing the ventilator, and generates information regarding presence or absence of laryngeal edema of the subject based on the acquired laryngeal airway diameter or the acquired signal value of the larynx.

9. The dynamic analysis system according to claim 8, wherein the hardware processor generates, as the information regarding the presence or absence of laryngeal edema, information of comparison between the laryngeal airway diameter or the signal value of the larynx, which is acquired based on the image obtained by performing still image capturing or dynamic imaging of the airway of the subject within a predetermined time after removing the ventilator, and a laryngeal airway diameter or a signal value of the larynx, which is acquired based on an image obtained by performing still image capturing or dynamic imaging of the airway of the subject before wearing the ventilator, or statistical data of a laryngeal airway diameter in healthy subjects or a signal value of a larynx in radiographic images of healthy subjects.

10. The dynamic analysis system according to claim 2, wherein the pulmonary complication includes at least one of pneumothorax, pneumonia, atelectasis, pulmonary edema, and pleural effusion.

11. The dynamic analysis system according to claim 10, wherein the hardware processor generates, as information regarding presence or absence of pneumothorax of the subject, information in which at least an image of a maximum exhalation position and an image of a maximum inhalation position obtained by performing still image capturing or dynamic imaging of a chest of the subject while wearing the ventilator or within a predetermined time after removing the ventilator are subjected to frequency enhancement processing and arranged in a comparable manner.

12. The dynamic analysis system according to claim 10, wherein the hardware processor calculates information regarding sizes of left and right lung fields based on an image obtained by performing still image capturing or dynamic imaging of the chest of the subject while wearing the ventilator or within a predetermined time after removing the ventilator, and generates the calculated information as the information regarding the presence or absence of pneumothorax of the subject.

13. The dynamic analysis system according to claim 10, wherein the hardware processor calculates information of at least one of a signal value of a lung field region, a cardiothoracic ratio, and a lung field area from each of images obtained by performing still image capturing or dynamic imaging of a chest of the subject before and while wearing the ventilator and generates, as information regarding presence or absence of pneumonia, atelectasis, pulmonary edema, or pleural effusion of the subject, information indicating a temporal change between the calculated information and information calculated based on an image obtained by performing still image capturing or dynamic imaging of the chest of the subject before wearing the ventilator or while wearing the ventilator in the past.

14. The dynamic analysis system according to claim 2, wherein the cardiac complication is heart failure.

15. The dynamic analysis system according to claim 14, wherein the hardware processor calculates information of at least one of information regarding blood flow in a lung field region and a cardiothoracic ratio based on an image obtained by performing still image capturing or dynamic imaging of a chest of the subject while wearing the ventilator and generates, as information regarding presence or absence of heart failure of the subject, information indicating a temporal change between the calculated information and information calculated based on an image obtained by performing still image capturing or dynamic imaging of the chest of the subject before wearing the ventilator or while wearing the ventilator in the past.

16. A non-transitory storage medium storing a computer readable program that is executable by a computer of a dynamic analysis system comprising a radiographic imaging system including a radiation generator that emits radiation and a flat panel detector that detects emitted radiation, the radiographic imaging system being operable to perform radiographic imaging of a subject, the program being executable by the computer to cause the computer to perform functions comprising:

receiving order information specifying an evaluation item related to evaluating complications caused by a subject wearing a ventilator; and executing, in accordance with the received order information, an evaluation process specified by the evaluation item, the evaluation process including at least one of an airway complication evaluation process, a pulmonary complication evaluation process, or a cardiac complication evaluation process, wherein executing the evaluation process comprises:

control the radiographic imaging system to perform radiographic imaging of the subject to acquire a still or dynamic radiographic image of a target region of the subject at least while wearing a ventilator or within a predetermined time after removing the ventilator, in accordance with the evaluation process specified by the evaluation item;

detecting, in the acquired radiographic image, a predetermined anatomical structure related to the specified evaluation process by performing image processing including at least one of edge detection, frequency enhancement, template matching, machine learning, or blood flow analysis;

calculating, based on the performed image processing, a first feature amount of the predetermined structure related to the evaluation process;

acquiring a second feature amount of the predetermined structure calculated from a radiographic image of the airway of the same subject captured before the subject was wearing the ventilator, the second feature amount being calculated using the same processing used to calculate the first feature amount;

generating comparison information by comparing the first feature amount with the second feature amount;

generating information regarding presence or absence of complications related to the ventilator of the subject based on the generated comparison information, in accordance with the specified evaluation process;

displaying an evaluation screen in which the generated information is displayed together with at least the first and second feature amounts and the radiographic image from which the first feature amount was calculated; and generating and outputting an audio or visual alert when a difference between the first feature amount and the second feature amount exceeds a threshold value set in advance.

\* \* \* \* \*